United States Patent

Nagasawa et al.

Patent Number: 4,894,438
Date of Patent: Jan. 16, 1990

[54] SYNTHETIC PEPTIDIC SUBSTRATE FOR DETERMINATION OF TRYPSIN AND $\alpha_1$-ANTITRYPSIN

[75] Inventors: Takeshi Nagasawa, Urawa; Yuko Gemba, Fukushima; Yoshio Nakamura; Katsumasa Kuroiwa, both of Koriyama, all of Japan

[73] Assignee: Nitto Boseki Co., Ltd., Japan

[21] Appl. No.: 934,249

[22] Filed: Nov. 21, 1986

[30] Foreign Application Priority Data

Nov. 26, 1985 [JP] Japan ................ 60-265388

[51] Int. Cl.$^4$ ............................... C07K 5/08
[52] U.S. Cl. ........................ 530/331; 435/7; 435/27
[58] Field of Search ................. 530/331, 317

[56] References Cited

U.S. PATENT DOCUMENTS

| | | | |
|---|---|---|---|
| 3,801,562 | 4/1974 | Benneville | 530/331 |
| 3,886,136 | 5/1975 | Claeson et al. | 530/331 |
| 4,137,225 | 1/1979 | Af Ekenstam et al. | 530/331 |
| 4,257,940 | 3/1981 | Fujii et al. | 530/331 |
| 4,409,140 | 10/1983 | Smith et al. | 530/331 |
| 4,428,874 | 1/1984 | Svendsen | 530/331 |
| 4,452,736 | 6/1984 | Nagasawa et al. | 530/331 |
| 4,457,866 | 7/1984 | Karges et al. | 530/331 |

OTHER PUBLICATIONS

Chem. Abstracts, vol. 92, 1980, 159413h.
Acta Medica Scandinavica, Supp. 432, Studies in $\alpha_1$-antitrypsin deficiency, Eriksson, 1965, pp. 41-75.

Primary Examiner—Delbert R. Phillips
Assistant Examiner—T. Wessendorf
Attorney, Agent, or Firm—Darby & Darby

[57] ABSTRACT

A synthetic peptide of the formula:

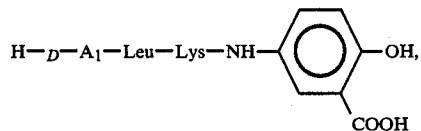

wherein $A_1$ is Pro or Ala, is excellent in solubility in water and substrate specificitity and is suitable as a substrate for determining trypsin and $\alpha_1$-antitrypsin.

3 Claims, 1 Drawing Sheet

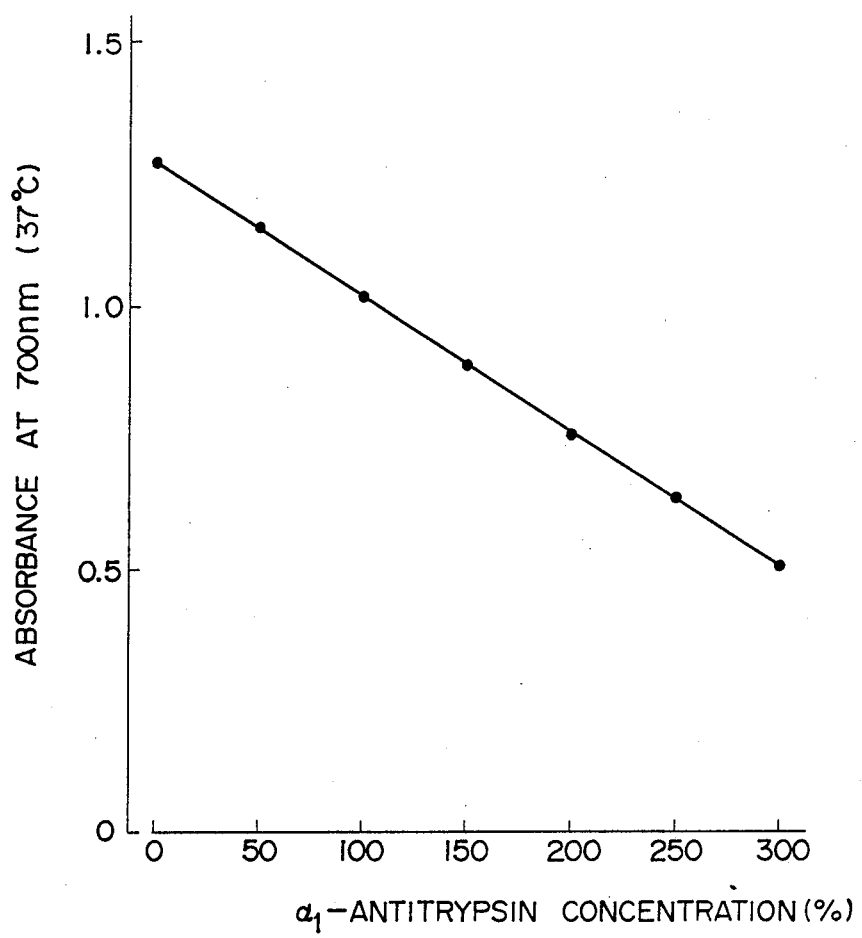

SYNTHETIC PEPTIDIC SUBSTRATE FOR DETERMINATION OF TRYPSIN AND $\alpha_1$-ANTITRYPSIN

BACKGROUND OF THE INVENTION

This invention relates to a synthetic peptidic substrate having a color-producible and fluorescence-emittable group suitable for the determination of trypsin and $\alpha_1$-antitrypsin. The substrate of this invention is remarkably high in the selectivity compared with known substrates and thus suitable for the determination of trypsin. Further, the substrate of this invention can be used for studies of reactions wherein the function of trypsin is inhibited or trypsin is consumed, or studies of factors pertaining to these reactions, particularly for the determination of $\alpha_1$-antitrypsin.

$\alpha_1$-antitrypsin (hereinafter referred to as "$\alpha_1$-AT") is a glycoprotein having a molecular weight of about 51,000 and contained in normal serum in a concentration of 160 to 350 mg/dl. A major function of $\alpha_1$-AT is to combine with proteases such as trypsin, chymotrypsin, thrombin, kallikrein, etc., and further with elastase derived from white blood cells, collagenase, etc. to form stable complexes, which results in neutralizing or inhibiting the functions of these proteases.

$\alpha_1$-AT is also called as an acute phase reactant and increases remarkably its content in serum in acute inflammation diseases, after surgical operations or destruction of tissues. The content of $\alpha_1$-AT is also increased by administration of estrogen or insulin, and in pregnancy, but decreased by serious liver function disorder such as liver cirrhosis, malignant hepatitis and low nutritive conditions. Further, since it has recently been known that the $\alpha_1$-antitrypsin content is also increased by a malignant tumor, $\alpha_1$-AT is expected to be used as a marker for related tumors.

Specificity of qualitative change of $\alpha_1$-AT has been noticed since a report of complication of pulmonary emphysema and an $\alpha_1$-antitrypsin deficiency [S. Eriksson: Acta Medica Scandinavica, Supplementum 432, pp. 41–75 (1965)]. Since that time, a relationship between $\alpha_1$-AT and chronic obstructive lung disease has gradually become clear. Therefore, it is significant that $\alpha_1$-AT which has been noticed clinically can be determined simply and precisely.

The determination of $\alpha_1$-AT in serum can be carried out by measuring inhibitory ability of trypsin activity. That is, when trypsin is added to serum, a part of the trypsin added is deactivated depending on the amount of $\alpha_1$-AT. Thus, the activity of remaining trypsin is measured to determine $\alpha_1$-antitrypsin.

As substrates for determining trypsin, there were used formerly proteins such as gelatin, hemoglobin, etc. But after Bergman et al reported that trypsin had amidase and esterase functions in addition to the protein decomposition function in 1939, various synthetic substrates (e.g. Bz-$L$-Arg-OEt, Tos-$L$-Arg-OMe, Bz-$DL$-Arg-pNA, Tos-$L$-Arg-pNA, etc.) have been used in the determination based on the amido bond or the ester bond of arginine. But these synthetic substrates had problems in the specificity of substrates and solubility in water or buffer solutions. As substrates for determining trypsin, there have further been developed Z-Val-Gly-Arg-pNA (CHR-TRY, a trade name, mfd. by Pentapharm A.G.), etc. (U.S. Pat. No. 4,278,762) and aminomethylcoumarin (AMS) which can emit fluorescence after freed [Smith et al.: Chemical Abstr. 92: 159413h (1980)]. In the above, Bz means benzoyl, Arg araginyl, OEt ethoxy, Tos p-toluenesulfonyl, OMe methoxy, pNA para-nitroanilide, Z a benzyloxycarbonyl group, Val valyl, and Gly glycyl.

On the other hand, in the determination of $\alpha_1$-AT in serum by using a color-developable substrate, if cross reactions take place with proteases other than trypsin such as plasmin, thrombin, factor Xa, urokinase, etc. which are expected to be present in the serum, precise measurement cannot be expected.

The above-mentioned CHR-TRY which is the best substrate for the determination of trypsin is not always satisfactory in the substrate specificity. That is, it is known that CHR-TRY reacts considerably with thrombin, plasmin, factor Xa, urokinase, etc. other than trypsin. Further, in the process of colorimetric determination of a yellow color of p-nitroanilide produced by using CHR-TRY as a substrate, influences of serum components cannot be prevented.

The amount of $\alpha_1$-AT in serum is usually as large as 160 to 350 mg/dl, which value is about 10 times as large as that of $\alpha_2$-macroglobulin ($\alpha_2$-M) in a molar concentration, $\alpha_2$-M being also present in serum. Further, $\alpha_1$-AT easily reacts with various inflammation stimuli to increase the amount thereof about 2 to 4 fold in the serum. In order to determine $\alpha_1$-AT which is present in a large amount and changes in amounts greatly in the following method, there are many problems:

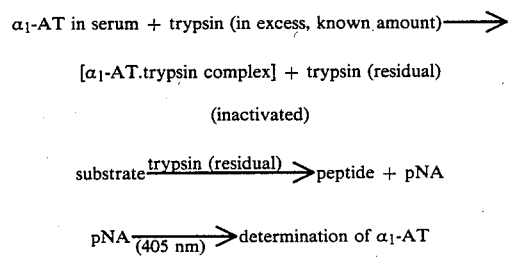

That is, in order to measure $\alpha_1$-AT precisely with a serum dilution rate of about 100 to 150 times usually used in this art, a large amount of trypsin should be used together with a considerably large amount of substrate. In contrast, in order to carry out the assay by using suitable amounts of the enzyme, and substrate in a suitable measuring range, it is necessary to dilute the serum about 500 to 1000 times. But such a high dilution rate is undesirable since procedures in daily examination becomes complicated and easily causes errors in measurement, the reactivity with $\alpha_1$-AT and trypsin changes, influence of $\alpha_2$-macroglobulin ($\alpha_2$-M) becomes not negligible, and precise measurement becomes difficult. In order to make the serum dilution rate about 100 to 150 times, it is necessary to develop new substrates which have proper reactivity with trypsin and high solubility in water or buffer solutions.

SUMMARY OF THE INVENTION

It is an object of this invention to provide a synthetic peptide suitable for determination of trypsin and $\alpha$-antitrypsin, particularly for determination of $\alpha_1$-AT, with a suitable serum dilution rate, having high specificity for trypsin and sufficient solubility in the measuring system.

This invention provides a synthetic peptide of the formula:

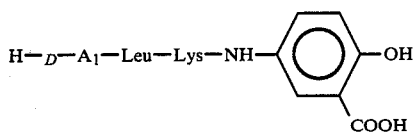

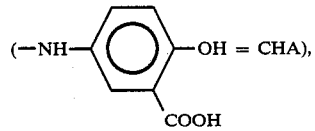

wherein $A_1$ is a prolyl (Pro) or alanyl (Ala) group; Leu is a leucyl group; and Lys is a lysyl group, or an acid addition salt thereof.

This invention also provides a process for using a synthetic peptide of the formula:

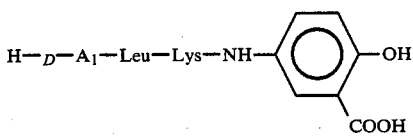

wherein $A_1$, Leu and Lys are as defined above, or an acid addition salt thereof, as a substrate for determining trypsin or $\alpha_1$-antitrypsin.

This invention further provides a process for determining $\alpha_1$-antitrypsin which comprises adding a trypsin solution having a known amount of trypsin to a sample solution, incubating the resulting mixture, adding a substrate solution containing as a substrate a synthetic peptide of the formula:

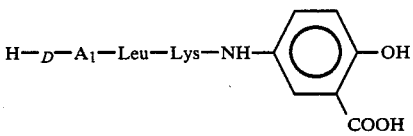

wherein $A_1$, Leu and Lys are as defined above, or an acid addition salt thereof, to the mixture, incubating the resulting mixture, adding a coupler to the mixture, and measuring a color produced colorimetrically.

BRIEF DESCRIPTION OF THE DRAWING

The attached drawing is a calibration curve for determining $\alpha_1$-AT.

DESCRIPTION OF THE PREFERRED EMBODIMENTS

The synthetic peptide of this invention is represented by the formula:

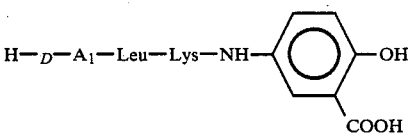

wherein $A_1$ is a prolyl (Pro) or alanyl (Ala) group; Leu is a leucyl group; and Lys is a lysyl group, or an acid addition salt thereof. Since the synthetic peptide of the formula (I) (hereinafter, the peptide of the formula (I) also includes an acid addition salt thereof) has remarkably hydrophilic groups such as a hydroxyl group and a carboxyl group at the color-producible moiety it has predominant dissolving properties in water.

The synthetic peptide of the formula (I) also has excellent substrate specificity for trypsin compared with prior art substrates such as CHR-TRY (Z-Val-Gly-Arg-pNA). This can be shown by the following Table 1 wherein relative reactivities of substrates with various proteases such as trypsin (Try), thrombin (TH), plasmin (PL), factor Xa (FXa), kallikrein (KL), and urokinase (UK) are shown by taking the reactivity of a substrate represented by the formula:

$$\text{H-}_D\text{-Pro-Leu-Lys-pNA} \tag{II}$$

with proteases as 100. The substrate of the formula (II) is only different from the synthetic peptide of the formula (I) in the chromophic group.

TABLE 1

| Protease | Substrate | | |
|---|---|---|---|
| | CHR—TRY | PS-1188N | PS-1188 |
| Try | 1626 (2.601) | 100 (0.160) | 86 (0.314) |
| TH | 2200 (0.066) | 100 (0.003) | 0 (0.0) |
| PL | 43 (0.057) | 100 (0.134) | 3 (0.008) |
| FXa | 2114 (0.148) | 100 (0.007) | 37 (0.006) |
| KL | 74 (0.029) | 100 (0.039) | 2 (0.002) |
| UK | (0.112) | (0.0) | (0.001) |

(Note)
Initial substrate concentration: 2 mmol
Values in parentheses are measured optical density values.
CHR—TRY = Z—Val—Gly—Arg—pNA
PS-1188N = H—$_D$-Pro—Leu—Lys—pNA
PS-1188 = H—$_D$-Pro—Leu—Lys—CHA
Detailed measuring conditions are described in Example 3 mentioned below.

As is clear from Table 1, the substrate PS-1188, one substrate of this invention having CHA as the color producible moiety, is remarkably low in the reactivity with thrombin, plasmin, factor Xa, kallikrein and urokinase. For example, the relative reactivity is 0% in the case of thrombin, 3% in the case of plasmin, 37% in the case of factor Xa and 2% in the case of kallikrein. These values mean that the substrate PS-1188 of this invention is remarkably improved in the selectivity compared with the prior art CHR-TRY wherein the relative reactivity is 2200% in the case of thrombin, 43% in the case of plasmin, 2114% in the case of factor Xa and 74% in the case of kallikrein.

Since the synthetic peptide of the formula (I) is excellent in water solubility and substrate specificity, it can be used for determining trypsin or $\alpha_1$-antitrypsin with high precision. Considering the substrate specificity shown in Table 1, the synthetic peptide of the formula (I) is particularly suitable for determining $\alpha_1$-AT.

The principle of the determination of trypsin or $\alpha_1$-antitrypsin is to react the synthetic peptide of the formula (I) with trypsin to produce a colored substance obtained by reacting the released 3-carboxy-4-hydroxyaniline with pentacyanoamine ferroate (PCAF), or a suitable coupler (by oxidative coupling), and to conduct colorimetrical determination.

Alternatively, the released 3-carboxy-4-hydroxy-aniline is excited by an exciting wavelength of 328 nm and the emitted fluorescence wavelength of 540 nm is measured by conventional fluorometric analysis. The fluorometric analysis is suitable for the determination of trypsin activity.

The colorimetrical determination method mentioned above is particularly suitable for determining $\alpha_1$-AT. $\alpha_1$-AT in serum can be determined, for example, as follows:

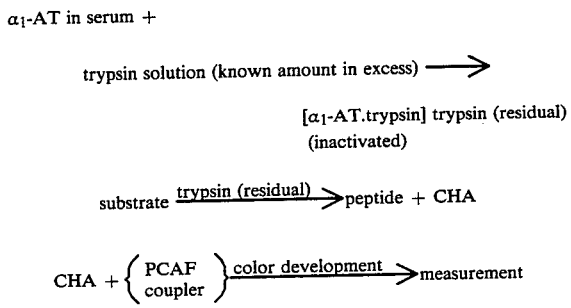

In the above procedures, the substrate is reacted with trypsin in a buffer solution having a pH of 8.0 to 8.7.

In order to form a colored substance, the 3-carboxy-4-hydroxy-aniline released from the synthetic peptide of the formula (I) is reacted with sodium pentacyanoamine ferroate (the pentacyanoamine ferroate method), or subjected to oxidative coupling with a coupler (the oxidative coupling method). As the coupler, there can be used aniline series compounds such as N,N-diethylaniline, N,N-diethyl-m-toluidine, etc., in the case of the color development in an acidic side, and phenolic compounds such as phenol, naphthol, thymol, cresol, etc., in the case of the color development in an alkaline side.

In the oxidative coupling, an oxidant such as hydrogen peroxide, persulfates, metaperiodates, and the like oxidants is used. Among them, the use of metaperiodate is preferable.

The resulting colored substances have maximum absorption wavelengths in the range of 560 to 770 nm depending on the coupler and the like used. The color developed is hardly changed by the temperature change and stable, so that it is suitable for determining the trypsin activity. The synthetic peptide of the formula (I) is hardly influenced by other enzymes in serum as mentioned above. Further, since the colorimetric determination is conducted at a wavelength of 560 nm or more in this invention, highly precise measured results can be obtained without being affected by the impurities in the sample compared with the p-nitroanilide series compounds (pNA, etc.) which are measured by using a wavelength of 560 nm or less.

As mentioned above, the synthetic peptide of the formula (I) is by far superior as the substrate to known substrates in the determination of $\alpha_1$-AT.

The synthetic peptide of the formula (I) can by synthesized by conventional processes. For example, the color producible moiety (CHA) is first bonded to a lysyl (Lys) group, and further coupled to amino acid components one after another. It is also possible to synthesize an N-terminal dipeptide fragment first, followed by bonding to a lysyl group having the color producible moiety (CHA).

As an $\alpha$-amino protecting group of amino acids used as reactants, there can preferably be used a carbobenzoxy group, a t-butyloxycarbonyl group or its relating groups such as a p-methoxycarbonyl group, a p-nitrocarbonyl group, or a p-methoxyphenylazolcarbobenzoxy group.

As a protecting group for the $\epsilon$-amino group of lysin, it is preferable to use a carbobenzoxyl group or a t-butyloxycarbonyl group.

The coupling of two amino acids, or the coupling of a dipeptide to an amino acid can be carried out by activating the $\alpha$-carboxyl group. For example, using N-hydroxysuccinicimide, p-nitrophenol, trichlorophenol, 4,6-dimethylpyrimidyl-2-thiol etc., the coupling can be carried out.

The activation for the ester derivative mentioned above can preferably be carried out in the presence of a carbodiimide such as N,N-dicyclohexylcarbodiimide (DCC).

The synthetic peptide of the formula (I) can be used in the form of an acid addition salt thereof. As the acid for the acid addition salt, there can be used a mineral acid such as hydrochloric acid, sulfuric acid, etc., an organic acid such as acetic acid, trifluoroacetic acid, etc.

This invention is illustrated by way of the following Examples, wherein the following abbreviations and analytical conditions were employed.

① Abbreviations

Lys=lysin, lysyl
Pro=proline, prolyl
Ala=alanine, alanyl
Leu=leucine, leucyl
Z=benzyloxycarbonyl
BOC=t-butyloxycarbonyl
-SDP=4,6-dimethylpyrimidyl-2-thio
DMF=dimethylformamide
MeOH=methanol
BuOH=n-butanol
AcOH=acetic acid
AcOEt=ethyl acetate
NEM=N-ethylmorpholine
-pNA=p-nitroanilide
-CHA=3-carboxy-4-hydroxy-anilide
TLC=thin-layer chromatography
GPC=gel-permeation chromatography The amino acids means L-isomers unless otherwise specified.

② Conditions for TLC

There was used a silica gel $F_{254}$ (mfd. by Merck & Co., Inc.) plate.

Solvent $Rf_1$=CHCl$_3$:MeOH:AcOH:H$_2$O=80:20:2.5:5
$Rf_2$=n-BuOH:AcOH:H$_2$O=4:1:1
$Rf_3$=n-BuOH:AcOH:H$_2$O=4:1:5

③ GPC

There was used polyvinyl gel (Toyo pearl HW 40F, a trade name, mfd. by Toyo Soda Mfg. Co., Ltd.) was used.

EXAMPLE 1

Synthesis of H-$_D$-Pro-Leu-Lys-CHA (A) BOC-Leu-Lys(Z)-CHA

In 200 ml of 1.5N NEM/DMF mixture, 45.2 g (0.2 mol) of H-Lys(Z)-CHA.HCl was dissolved, and 35.3 g (0.1 mol) of BOC-Leu-SDP was added thereto at 0° to 5° C. The reaction was carried out at room temperature for 18 hours. After the reaction, the solvent was removed by distillation under reduced pressure. The residue was dissolved in 1500 ml of AcOEt and washed with 500 ml of a cooled 5% HCl solution twice, and 500 ml of a saturated saline solution twice, followed by decoloration and drying over anhydrous magnesium sulfate and active carbon. After drying, the magnesium sulfate and active carbon were filtered and the solvent was removed by distillation under reduced pressure to yield crude BOC-Leu-Lys(Z)-CHA. This was recrystallized from a mixed solvent of AcOEt/ether/n-hexane to give 35.9 g (57.1%) of BOC-Leu-Lys(Z)-CHA.

$Rf_1 = 0.51$, m.p. 110°–119.5° C.
$[\alpha]_D^{20}$ −13.0 (c=1, DMF).
Elementary analysis ($C_{32}H_{44}N_4O_9 \cdot \frac{1}{2}H_2O$):

|  | C (%) | H (%) | N (%) |
|---|---|---|---|
| Found | 60.42 | 7.10 | 8.77 |
| Calcd. | 60.27 | 7.11 | 8.79 |

(B) Z-$_D$-Pro-Leu-Lys(Z)-CHA

In 90.8 ml of 2N HCl/AcOH, 22.8 g (36.3 mmol) of BOC-Leu-Lys(Z)-CHA was dissolved and reacted at room temperature for 2 hours. After the reaction, deposited crystals were reprecipitated in 1000 ml of ether, filtered and dried to yield 20.1 g (98.0%) of H-Leu-Lys(Z)-CHA.HCl.

$Rf_2 = 0.68$, m.p. 147°–157.5° C.
$[\alpha]_D^{20}$ −0.8 (c=0.5, MeOH).

In 41 ml of 1.5N NEM/DMF mixture, 11.6 g (20.5 mmol) of H-Leu-Lys(Z)-CHA.HCl was dissolved and 20 ml of DMF solution containing 7.6 g (20.5 mmol) of Z-$_D$-Pro-SDP was added thereto at 0° to 5° C. The reaction was carried out at room temperature for 15 hours. After the reaction, the reaction solution was diluted with 1000 ml of AcOEt and washed with 500 ml of 5% HCl twice and 500 ml of a saturated saline solution twice, followed by decoloration and drying over anhydrous magnesium sulfate and active carbon. After drying, the magnesium sulfate and active carbon were filtered and the solvent was removed by distillation under reduced pressure to yield crude Z-$_D$-Pro-Leu-Lys(Z)-CHA. This was recrystallized from DMF/AcOEt/ether to give 8.7 g (55.6%) of Z-$_D$-Pro-Leu-Lys(Z)-CHA.

$Rf_1 = 0.53$, m.p. 230.5°–235.0° C.
$[\alpha]_D^{20}$ +4.0 (c=1, DMF).
Elementary analysis ($C_{40}H_{49}N_5O_{10}$):

|  | C (%) | H (%) | N (%) |
|---|---|---|---|
| Found | 62.89 | 6.56 | 9.31 |
| Calcd. | 63.23 | 6.50 | 9.22 |

(C) H-$_D$-Pro-Leu-Lys-CHA.2HCl

In a mixed solvent of 225 ml of MeOH, 61.2 ml of water and 13.8 ml of 1N HCl, 3.5 g (4.6 mmol) of Z-$_D$-Pro-Leu-Lys(Z)-CHA was suspended and 2 g of palladium black was added thereto. Catalytic reduction was carried out at 30° C. for 6 hours. After the reaction, the catalyst was removed by filtration and the solvent was removed by distillation under reduced pressure. The residue was purified by using Toyo pearl HW40F column and MeOH as a developing solvent to yield 2.2 g (83.4%) of H-$_D$-Pro-Lys-CHA.2HCl.

$Rf_3 = 0.17$, m.p. 203° C. (decomposed).
$[\alpha]_D^{20}$ −30.0 (C=0.5, MeOH).
Elementary analysis ($C_{24}H_{39}N_5O_6Cl_2 \cdot H_2O$):

|  | C (%) | H (%) | N (%) |
|---|---|---|---|
| Found | 49.67 | 7.17 | 11.96 |
| Calcd. | 49.49 | 7.09 | 12.02 |

EXAMPLE 2

H-$_D$-Ala-Leu-Lys-CHA.2HCl (PS-1181) was synthesized in the same manner as described in Example 1, except for using Z-$_D$-Ala-SDP in place of Z-$_D$-Pro-SDP. Properties of PS-1181 were as follows:

m.p. 196.5°–210° C.
$Rf_3 = 0.26$.
$[\alpha]_D^{20}$ −48.0 (C=0.5, MeOH).
Elementary analysis ($C_{22}H_{37}N_5O_6Cl_2 \cdot \frac{1}{2}H_2O$):

|  | C (%) | H (%) | N (%) |
|---|---|---|---|
| Found | 48.38 | 6.95 | 12.94 |
| Calcd. | 48.26 | 7.00 | 12.79 |

EXAMPLE 3

The synthetic peptides obtained in Examples 1 and 2 were subjected to a substrate specificity test by reacting with various enzymes under the following conditions.

(1) substrate solution: 10 mmol/l (concentration)
(2) buffer solution: tris-HCl buffer Concentrations of NaCl, and CaCl$_2$ and pH (at 25° C.) were adjusted as shown in Table 2 depending on enzymes to be reacted:

TABLE 2

| Enzyme | Buffer Solution | | | |
|---|---|---|---|---|
|  | Tris (mmol/l) | NaCl (mmol/l) | CaCl$_2$ (mmol/l) | pH (25° C.) |
| Trypsin (Try) | 100 | 150 | 0 | 8.0 |
| Thrombin (TH) | 50 | 150 | 0 | 8.5 |
| Plasmin (PL) | 50 | 150 | 0 | 7.8 |
| Factor Xa (FXa) | 50 | 250 | 5 | 8.3 |
| Kallikrein (KL) | 50 | 150 | 0 | 7.8 |
| Urokinase | 50 | 150 | 0 | 8.2 |

(3) Enzyme used are shown in Table 3.

TABLE 3

| Enzyme | Origin | Manufacturer | Lot No. | Unit |
|---|---|---|---|---|
| Trypsin | Bovine | Worthington | 31M771 | 10 μg/ml |
| Thrombin | Bovine | Mochida Pharmaceutical Co., Ltd. | 65146 | 4.0 NIH/ml |
| Plasmin | Human | Green Cross Corp. | PL-35 | 0.25 cu/ml |
| Factor Xa | Bovine | Sigma Chem. Co. | 73F-9450 | 0.4 U/ml |
| Kallikrein | Porcine | Sigma Chem. Co. | 32F-0810 | 1.0 U/ml |
| Urokinase | Human | Mochida Pharma- | 2A239 | 1000 U/ml |

TABLE 3-continued

| Enzyme | Origin | Manufacturer | Lot No. | Unit |
|---|---|---|---|---|
|  |  | ceutical Co., Ltd. |  |  |

(4) Reaction stopper solution in the case of pNA: 10% acetic acid
(5) Color producing reagent for CHA: sodium pentacyanoamine ferroate Measuring Method The buffer solution in an amount of 0.3 ml and 0.1 ml of an enzyme solution were placed in a test tube made of hard glass treated with silicon or a test tube made of a plastic (polystyrene) and preheated for 5 minutes in a constant temperature bath maintained at 37° C. Then, 0.1 ml of a substrate solution was added to the test tube and incubated at 37° C. for just 5 minutes. Subsequently, 2.0 ml of the reaction stopper solution (in the case of pNA) or the color producing reagent (in the case of CHA) was added to the reaction solution to terminate the enzymatic reaction. After allowing to stand at 37° C. for 10 minutes, absorbance (optical density) at 405 nm (in the case of pNA) or at 700 nm (in the case of coupled CHA) was measured. The initial substrate concentration was 2 mmol/l.

The results are shown in Table 4.

TABLE 4

| Enzyme | PS-1188 (Example 1) | PS-1181 (Example 2) | CHR—TRY (Comparison) | PS-1188N (Reference) |
|---|---|---|---|---|
| Trypsin | 0.314 | 0.393 | 2.601 | 0.160 |
| Thrombin | 0.0 | 0.0 | 0.066 | 0.003 |
| Plasmin | 0.008 | 0.003 | 0.057 | 0.134 |
| Factor Xa | 0.006 | 0.008 | 0.148 | 0.007 |
| Urokinase | 0.001 | 0.003 | 0.112 | 0.0 |
| Kallikrein | 0.002 | 0.006 | 0.029 | 0.032 |
| Wavelength | 700 nm | | 405 nm | |

Note:
PS-1188: H—$_D$-Pro—Leu—Lys—CHA.2HCl
PS-1181: H—$_D$-Ala—Leu—Lys—CHA.2HCl
CHR—TRY: Z—Val—Gly—Arg—pNA
PS-1188N: H—$_D$-Pro—Leu—Lys—pNA As is clear from Table 4, the synthetic peptides of this invention are excellent in substrate specificity compared with CHR-TRY.

EXAMPLE 4

Using the substrate synthesized in Example 1, a calibration curve for determining $\alpha_1$-AT as shown in the attached drawing was prepared under the following conditions:
(1) Substrate solution concentration: 10 mmol/l
(2) Buffer solution:
 tris-HCl 200 mM
 NaCl 150 mM
 pH=9.0
(3) Enzyme solution: trypsin 9 μg/ml
(4) Solution for dissolving enzyme:
 glycerin 25% by wt.
 albumin 1 mg/ml
 pH=3.0
(5) Standard serum: pooled serum of normal person
(6) Color producing reagent solution: sodium pentacyanoamine ferroate solution Measuring Method The standard serum was diluted with the buffer solution in 150-fold and defined as the 100% concentration standard solution. On the other hand, the buffer solution was used as the 0% concentration standard solution.

A serum in an amount of 0.1 ml was placed in a test tube made of hard glass treated with silicon or made from a plastic and preheated for 5 minutes in a constant temperature bath maintained at 37° C. Then, 0.4 ml of trypsin solution was added thereto and incubated for 5 minutes. Subsequently, 0.5 ml of the substrate solution was added to the test tube and incubated at 37° C. for just 5 minutes. Then, 2.5 ml of the color producing reagent solution was added to the reaction solution to terminate the enzymatic reaction. After allowed to stand at 37° C. for 10 minutes, absorbance at 700 nm was measured.

Using the calibration curve of the attached drawing, the activity of $\alpha_1$-AT in serum can be determined with high precision without suffering from interferences of other co-existing enzymes.

What is claimed is:
1. A synthetic peptide of the formula:

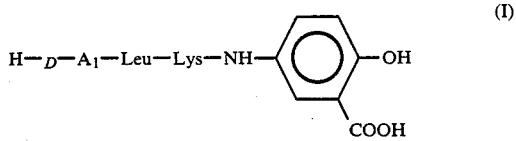

(I)

wherein $A_1$ is a prolyl (Pro) or alanyl (Ala) group; Leu is a leucyl group; and Lys is a lysyl group, or an acid addition salt thereof.

2. A synthetic peptide according to claim 1, which is

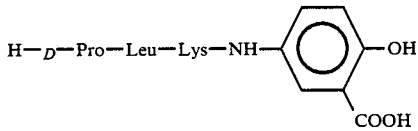

or an acid addition salt thereof.

3. A synthetic peptide according to claim 1, which is

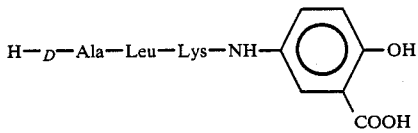

or an acid addition salt thereof.

* * * * *